United States Patent
Sarama et al.

(10) Patent No.: US 6,310,227 B1
(45) Date of Patent: Oct. 30, 2001

(54) REDUCED CALORIE COOKING AND FRYING OILS HAVING IMPROVED HYDROLYTIC STABILITY, AND PROCESS FOR PREPARING

(75) Inventors: Robert Joseph Sarama, Loveland; John Keeney Howie, Oregonia, both of OH (US); Reginald Sebastian Clay, Charlottesville, VA (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/355,543

(22) PCT Filed: Jan. 9, 1998

(86) PCT No.: PCT/US98/00608

§ 371 Date: Oct. 6, 1999

§ 102(e) Date: Oct. 6, 1999

(87) PCT Pub. No.: WO98/33803

PCT Pub. Date: Aug. 6, 1998

Related U.S. Application Data

(60) Provisional application No. 60/036,694, filed on Jan. 31, 1997.

(51) Int. Cl.$^7$ .............................. C11B 3/00; C11B 7/00; C11B 13/00
(52) U.S. Cl. .......................................... 554/191; 554/227
(58) Field of Search ...................... 554/191, 227

(56) References Cited

U.S. PATENT DOCUMENTS

| | | | |
|---|---|---|---|
| 2,962,419 | 11/1960 | Minich | 167/81 |
| 3,579,548 | 5/1971 | Whyte | 260/410.7 |
| 3,600,186 | 8/1971 | Mattson et al. | 99/1 |
| 3,932,532 | 1/1976 | Hunter et al. | 260/615 R |
| 3,963,699 | 6/1976 | Rizzi et al. | 260/234 R |
| 4,005,195 | 1/1977 | Jandacek | 424/180 |
| 4,005,196 | 1/1977 | Jandacek et al. | 424/180 |
| 4,334,061 | 6/1982 | Bossier, III | 536/119 |
| 4,508,746 | 4/1985 | Hamm | 426/601 |
| 4,517,360 | 5/1985 | Volpenhein | 536/119 |
| 4,518,772 | 5/1985 | Volpenhein | 536/119 |
| 4,582,927 | 4/1986 | Fulcher | 560/201 |
| 4,840,815 | 6/1989 | Meyer et al. | 426/611 |
| 4,861,613 | 8/1989 | White et al. | 426/611 |
| 4,888,195 | 12/1989 | Huhn et al. | 426/601 |
| 4,954,621 | 9/1990 | Masaoka et al. | 536/119 |
| 4,968,791 | 11/1990 | Van der Plank | 536/119 |
| 4,973,681 | 11/1990 | Watanabe | 536/119 |
| 4,983,329 | 1/1991 | Cooper | 260/410.7 |
| 5,055,571 | 10/1991 | Van Lookeren | 536/124 |
| 5,071,975 | 12/1991 | Van der Plank et al. | 536/119 |
| 5,079,355 | 1/1992 | Meszaros Grechke et al. | 536/119 |
| 5,085,884 | 2/1992 | Young et al. | 426/611 |
| 5,175,323 | 12/1992 | Cooper | 554/164 |
| 5,254,227 | 10/1993 | Cawlfield et al. | 204/131 |
| 5,273,772 | 12/1993 | Cooper | 426/611 |
| 5,288,884 | 2/1994 | Cooper | 554/168 |
| 5,298,637 | 3/1994 | Cooper | 554/169 |
| 5,304,665 | 4/1994 | Cooper et al. | 554/149 |
| 5,306,514 | 4/1994 | Letton et al. | 426/531 |
| 5,306,516 | 4/1994 | Letton et al. | 426/531 |
| 5,362,894 | 11/1994 | Handwerker et al. | 554/169 |
| 5,374,446 | 12/1994 | Ferenz et al. | 426/611 |
| 5,387,429 | 2/1995 | Cooper | 426/611 |
| 5,399,728 | 3/1995 | Cooper | 554/149 |
| 5,399,729 | 3/1995 | Cooper et al. | 554/149 |
| 5,419,925 | 5/1995 | Seiden et al. | 426/611 |
| 5,422,131 | 6/1995 | Elsen et al. | 426/531 |
| 5,427,815 | 6/1995 | Ferenz | 426/611 |
| 5,451,416 | 9/1995 | Johnston et al. | 426/531 |
| 5,480,667 | 1/1996 | Corrigan et al. | 426/531 |
| 5,490,995 | 2/1996 | Corrigan | 426/531 |
| 5,512,313 | 4/1996 | Cooper et al. | 426/611 |
| 5,516,544 | 5/1996 | Sekula et al. | 426/611 |
| 5,534,284 | 7/1996 | Corrigan et al. | 426/531 |
| 5,589,217 | 12/1996 | Mazurek | 426/611 |
| 5,597,605 | 1/1997 | Mazurek | 426/611 |
| 5,603,978 | 2/1997 | White et al. | 426/611 |
| 5,641,534 | 6/1997 | White et al. | 426/611 |

FOREIGN PATENT DOCUMENTS

| | | | |
|---|---|---|---|
| 2020301 | 7/1990 | (CA) | C08K/5/10 |
| 148459 | 5/1981 | (DE) | C08G/18/06 |
| 236 288 A2 | 9/1987 | (EP) | A23D/5/00 |
| 233 856 B1 | 1/1994 | (EP) | A23D/9/00 |
| WO 97/22602 | 6/1997 | (WO) | C07D/307/935 |
| WO 98/33803 | 8/1998 | (WO) | C07H/13/06 |

OTHER PUBLICATIONS

*Chemical Engineers Handbook*, 6$^{th}$ Edition, 1984, pp. 21–77 to 21–79.
U.S. Ser. No. 08/797,018, filed Feb. 7, 1997, P&G Case No. 6506.
U.S. Ser. No. 09/355,542, filed Jul. 29, 1999, P&G Case No. 6502M2.

*Primary Examiner*—Deborah D. Carr
(74) *Attorney, Agent, or Firm*—Erich D. Hemm; Carl J. Roof

(57) ABSTRACT

The present invention relates to a process for preparing calorie cooking and frying oils, containing nondigestable polyol polyesters, and having improved color and improved stability against hydrolysis during frying. The process comprises, as a first step, treating a crude polyol polyester with an ion exchange ligand in an aqueous phase to convert diavalent metal soaps present in the crude polyol polyester to monovalent soaps. The monovalent soaps and ion exchange ligands are then removed from the treated polyol polyester to provide a cooking and frying oil which contains less than about 550 ppb divalent metal ions. Said oil, when further processed according to conventional industry standards will have a free fatty acid content of less than about 500 ppm. Preferably, the cooking and frying oils prepared according to the process of the present invention will further have a Lovibond red color of less than about 6, preferably less than about 4.

27 Claims, No Drawings

REDUCED CALORIE COOKING AND FRYING OILS HAVING IMPROVED HYDROLYTIC STABILITY, AND PROCESS FOR PREPARING

This application is a 371 of PCT/US98/00608, filed Jan. 9, 1998 and claims the benefit of U.S. Provisional application Ser. No. 60/036,694 filed Jan. 31, 1997.

TECHNICAL FIELD

The present invention relates to reduced calorie cooking and frying oils which comprise nondigestable polyol polyesters and which have improved stability against hydrolysis during frying and a process for preparing such oils.

BACKGROUND OF THE INVENTION

The food industry has recently focused considerable attention on the production of polyol fatty acid polyesters for use as low calorie fats in food products. As a result, there is a continuing need for processes which economically and efficiently produce a relatively high purity polyol fatty acid polyester.

Certain nondigestable polyol fatty acid polyesters have been found to be useful as low calorie substitutes for triglyceride oils. For example, Mattson et al., (U.S. Pat. No. 3,600,186, issued Aug. 17, 1971), discloses low calorie cooking and frying oils in which at least a part of the triglyceride oil is replaced by a nonabsorbable, nondigestable sugar fatty acid ester or sugar alcohol fatty acid ester having at least 4 fatty acid ester groups with each fatty acid having from 8 to 22 carbon atoms. Bernhardt, (European Patent Application 236,288, Published Sep. 9, 1987), and Bernhardt, (European Patent Application 233,856, Published Aug. 26, 1987), disclose certain intermediate melting polyol polyesters which can be used as replacements for at least a portion of the triglyceride oil in cooking and frying oils and which provide passive oil loss control. Blends of completely liquid polyol polyesters with completely solid polyol polyester hardstocks, preferably esterified with $C_{10}$ to $C_{22}$ saturated fatty acids (e.g., sucrose octastearate or octabehenate) have also been proposed in order to provide passive oil loss control. See, for example, Jandacek; U.S. Pat. No. 4,005,195 and Jandacek/Mattson, U.S. Pat. No. 4,005,196; both issued Jan. 25, 1977.

Another type of nondigestable polyol polyester composition which can be used to replace part or all of the triglyceride oil in cooking or frying oil comprises combinations of liquid polyol polyesters and certain types of solid particulate material selected so that the composition has an essentially flat Solid Fat (SFC) profile slope over the temperature range between room temperature and body temperature. Generally, the solid material in such composition is present as very small particles (1 micron or less) and at relatively low concentration. Frequently, such solid particulate material, which serves as a passive oil loss control agent, will be a solid polyol polyester that crystallizes into the desired especially small particles. Examples of polyol polyester compositions of this type, and of cooking and frying oils containing them, are described in Young, U.S. Pat. No. 5,085,884, issued Feb. 4, 1992; Letton et al, U.S. Pat. No. 5,306,514, issued Apr. 26, 1994, and Letton, et al, U.S. Pat. No. 5,422,131, issued Jun. 1, 1995; and U.S. Pat. No. 5,534,284 to Corrigan et al., issued Jul. 9, 1996.

To produce a polyol fatty acid polyester, a polyol can be reacted with a fatty acid lower alkyl ester in the presence of a basic catalyst. In general, polyols are readily soluble in an aqueous medium, e.g., water, while fatty acid lower alkyl esters are soluble in an organic medium. Thus, an emulsifier, solvent, phase transfer catalyst or a mixture thereof is usually required to bring the polyol and the fatty acid lower alkyl ester into physical contact so that they can react chemically. The resulting polyol fatty acid polyester is soluble in an organic medium.

Nondigestable polyol polyesters are typically prepared by a solvent-free, essentially two-step transesterification of the polyol (e.g., sucrose) with the fatty acid esters of an easily removable alcohol (e.g., fatty acid methyl esters). In the first step, a mixture of sucrose, methyl esters, alkali metal fatty acid soap and a basic esterification catalyst are heated to form a melt. In the second step, an excess of methyl esters are added to this melt which is then heated to convert the partial sucrose esters to more highly esterified sucrose polyester. See, for example, Rizzi et al, U.S. Pat. No. 3,963,699, issued Jun. 15, 1976; and Volpenheim, U.S. Pat. No. 4,517,360, issued May 21, 1985.

Alternatively, highly esterified polyol polyesters can be prepared by two stage solvent-based processes (see, for example, Masaoka et al, U.S. Pat. No. 4,954,621, issued Sep. 4, 1990) or one stage solvent-based or solvent-free processes (see, for example: Van der Plank U.S. Pat. No. 4,968,791, issued Nov. 6, 1990; Meszaros Grechke et al, U.S. Pat. No. 5,079,355, issued Jan. 7, 1992; or Van der Plank et al, U.S. Pat. No. 5,071,975, issued Dec. 10, 1991).

As can be appreciated, the product stream resulting from the reaction of a polyol to produce a polyol fatty acid polyester can therefore contain a variety of components in addition to the desired polyol fatty acid polyester. For example, residual reactants, e.g., unreacted fatty acid lower alkyl ester and/or unreacted polyol, emulsifier, solvent, phase transfer catalyst and/or basic catalyst can be present in the product stream. Additionally, there can be numerous by-products of the reaction itself. For example, numerous side reactions occur in addition to the transesterification of the polyol to form a polyol fatty acid polyester. Side reactions can include the breakdown of one chemical component into two or more by-products, and/or the initial reactants, catalysts, emulsifiers and solvents can chemically react with one another to form undesired by-products, for example, di- and tri-glycerides, beta-ketoesters, di-fatty ketones, and saturated and unsaturated fatty acids and/or soaps. These unsaturated and saturated fatty acids and soaps can result from the hydrolysis of the polyol polyester, and of the starting methyl esters. Additionally, the initial reactants and other reaction ingredients are often supplied with trace quantities of materials, e.g. trace metals, including calcium and magnesium ions, which are particularly undesirable in a final product which is intended for use as a food additive. Thus, the product stream resulting from the reaction of a polyol and a fatty acid lower alkyl ester can contain, in addition to the desired polyol fatty acid polyester, a variety of undesirable constituents as impurities which need to be substantially removed to yield the desired purified polyol fatty acid polyester. These impurities can contribute to instability and/or discoloration of the polyol polyester, especially during cooking or frying. In general, it is therefore necessary to further refine or purify the crude polyol fatty acid polyester reaction products resulting from such conventional synthesis.

Conventional purification methods include washing with water, extraction with organic solvents and/or "salting-out" treatments. U.S. Pat. No. 4,334,061 describes sucrose polyesters preparation in which the reaction product is washed using an aqueous alkaline solution of pH 7–12 in the presence of a polar organic solvent. Van Lookeren, U.S. Pat. No. 5,055,571, issued Oct. 8, 1991, discloses a process for the purification of crude polyol polyesters by contacting the polyol polyesters with alkali metal ions under alkaline conditions to reduce the level of alkali metal ions to less than 5 ppm calculated by weight of the polyol polyesters. In this process the monovalent soap level present in the crude polyol polyester is preferably reduced by centrifuging or "filtering off" crystallized soap and/or one or more washings with water at near neutral conditions.

Watanabe, U.S. Pat. No. 4,973,681, issued Nov. 27, 1990, describes a purification process for increasing the oxidative stability of a polyol polyester comprising contacting a polyol polyester with a polybasic oxy-acid (e.g., citric acid) and then separating the polyol polyester from the polybasic acid. The reference discloses that this process removes trace amounts of metal catalyst which may be present in the crude polyol polyester.

Even when nondigestable polyol polyesters are purified as described above, the are not as stable against hydrolysis during frying as conventional triglyceride oils. Therefore, cooking and frying oils that comprise these nondigestable polyol polyesters develop an off-flavor faster than triglyceride frying oils and often discolor more quickly. It would, therefore, be desirable to prepare nondigestable polyol polyester cooking and frying oils which are equivalent to triglyceride oil in terms of hydrolytic stability and color development. The more stable the polyol polyester composition, the longer the fry-life of these oils.

It has been discovered that, in addition to the monovalent soaps discussed above, polyol polyesters can contain a significant amount of divalent metal ion higher soaps (e.g., calcium soap), and further that these divalent and higher-valent metal soaps have a deleterious effect on the hydrolytic stability of the polyol polyesters when, in addition, there are free fatty acids are present. These divalent and higher-valent metal ions are usually introduced into the polyol polyester as contaminants of the starting methyl esters. Free fatty acids can come into the polyol polyester from the food being fried, or by hydrolysis of the polyol polyesters, or both.

Therefore, a continuing need exists to improve the separation and purification of a polyol fatty acid polyester reaction product stream, particularly resulting from the transesterification of a polyol. More specifically, it is desirable to provide an economical and efficient separation process which can remove divalent and higher-valent soaps, and trace metals such as calcium and magnesium, as well as fatty acid methyl esters and fatty acids.

SUMMARY OF THE INVENTION

Surprisingly, it has been found that it is possible to prepare reduced calorie cooking and frying oils comprising polyol polyesters which are equivalent to triglyceride oils in terms of hydrolytic stability by reducing these divalent and higher valent (polyvalent) soaps in the polyol polyesters. Preferably the level of polyvalent metal ion is reduced to about 550 ppb or less.

Without limiting the scope of the invention in any way, it is believed that the deleterious effect of a divalent metal ion soap on the stability of polyol polyester frying oils is due to the divalent soap promoting hydrolysis and thereby cause instability and discoloration by forming free fatty acids, which are soluble in the polyol polyester, and thus accumulate in the polyol fatty acid polyester.

The present invention relates to an improved nondigestable polyol polyester for use as reduced-calorie cooking and frying oils, and a process for preparing such oil, having improved color stability and improved stability against hydrolysis during frying. The oil preferably contains less than about 550 ppb divalent and higher (i.e. polyvalent) valent metal ions.

The process comprises the steps of 1) intimately mixing a) an aqueous wash solution phase which comprises an ion exchange ligand with b) a crude polyol polyester which comprises a polyvalent soap having a polyvalent ion; 2) ion exchanging the polyvalent ion from the polyvalent soap to the ion exchange ligand; 3) forming a monovalent soap; and 4) removing the polyvalent ion exchange ligand and the monovalent soap from the crude polyol polyester. The nondigestible polyol polyester made by the process of the invention preferably contains less than about 550 ppb divalent and higher valent metal ions. The cooking and frying oils prepared according to the process of the present invention much more slowly develop color impurities and free fatty acid contaminants than indigestible oils which have divalent soaps present at higher levels.

DETAILED DESCRIPTION OF THE INVENTION

Definitions

The term "nondigestible" means that only about 70% or less of the material can be digested by the body. Preferably, only about 20% or less of such materials can be digested. More preferably, only about 1% or less of such materials can be digested.

As used herein, the term "polyol" is intended to include any aliphatic or aromatic compound containing at least two free hydroxyl groups. Suitable polyols can be selected from the following classes: saturated and unsaturated straight and branch chain linear aliphatic, saturated and unsaturated cyclic aliphatics, including heterocyclic aliphatics, or mononuclear or polynuclear aromatics, including heterocyclic aromatics. Carbohydrates and non-toxic glycols are preferred polyols. Monosaccharides suitable for use herein include, for example, mannose, galactose, arabinose, xylose, ribose, apiose, rhamnose, psicose, fructose, sorbose, tagatose, ribulose, xylulose, and erthulose. Oligosaccharides suitable for use herein include, for example, maltose, kojibiose, nigerose, cellulose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar, alcohols are so closely related to the carbohydrates that they are also preferred for use herein. Natural sugar alcohols which are suitable for use herein are sorbitol, mannitol, and galactitol.

Particularly preferred classes of materials suitable for use herein include the monosaccarides, the disaccharides and sugar alcohols. Preferred unesterified polyols include glucose, fructose, glycerol, polyglycerols, sucrose, zylotol, and sugar ethers. A particularly preferred polyol is sucrose. Preferred unesterified polyols also include alkoxylated polyols such as alkoxylated glycerin, alkoxylated polyglycerols, sorbitol, alkoxylated polysaccarides, and linked alkoxylated polyols such as linked alkoxylated glycerins. Polyols may be alkoxylated with $C_3$–$C_6$ epoxides, such as propylene oxide, butylene oxide, isobutylene oxide, and pentene oxide, to produce epoxide-extended polyols having an epoxylation index minimum of at least about 2, preferably in the range of from about 2 to about 8, as described in U.S. Pat. No. 4,816,613, incorporated herein by reference. Polyols may be also alkoxylated with an epoxide, preferably a $C_3$–$C_{10}$ 1,2-alkylene oxide, in the presence of a ring-opening polymerization catalyst, as described in U.S. Pat. Nos. 5,399,729 and 5,512,313, incorporated herein by reference.

Suitable alkoxylated polyols for use herein are described in U.S. Pat. Nos. 4,983,329; 5,175,323; 5,288,884; 5,298,637; 5,362,894; 5,387,429; 5,446,843; 5,589,217; 5,597,605; 5,603,978 and 5,641,534, all incorporated herein by reference. Suitable alkoxylated polyols include alkoxylated sugar alcohols, alkoxylated monosaccharides, alkoxylated disaccharides, alkoxylated polysaccharides, alkoxylated $C_2$–$C_{10}$ aliphatic diols, and alkoxylated $C_3$–$C_{12}$ aliphatic triols. Preferred alkoxylated $C_3$–$C_{12}$ aliphatic triols are alkoxylated glycerols, more preferred are propoxylated glycerols, and particularly preferred are propoxylated glycerols having from about 3 to about 21 moles of propylene oxide per mole glycerol. Preferred alkoxylated polysaccharides are alkoxylated polysaccharides containing anhydromonosaccharide units, while more preferred are propoxylated polysaccharides containing anhydromonosaccharide units, as described in U.S. Pat. No. 5,273,772, incorporated herein by reference. Preferred linked alkoxylated glycerins include those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544.

As used herein the term "polyol fatty acid polyester" is intended to include any polyol, as defined herein, which has two or more of its hydroxyl groups esterified with fatty acid groups. Suitable polyol fatty acid polyesters include sucrose polyesters having on average at lease four, preferably at least about five, ester linkages per molecule sucrose; the fatty acid chains preferably have from about eight to about twenty-four carbon atoms. Liquid nondigestable oils include liquid polyol fatty acid polyesters (see Jandacek; U.S. Pat. No. 4,005,195; issued Jan. 25, 1977); liquid esters of tricarballytic acids (see Hamm; U.S. Pat. No. 4,508,746; Issued Apr. 2, 1985); liquid diesters of dicarboxylic acids such as derivatives of malonic and succinic acid (see Fulcher; U.S. Pat. No. 4,582,927; Issued Apr. 15, 1986); liquid triglycerides of alpha-branched chain carboxylic acids (see Whyte; U.S. Pat. No. 3,579,548; Issued May 18, 1971); liquid ethers and ether esters containing the neopentyl moiety (see Minich; U.S. Pat. No. 2,962,419; Issued Nov. 29, 1960); liquid fatty polyethers of polyglycerol (See Hunter et al; U.S. Pat. No. 3,932,532; Issued Jan. 13, 1976); liquid alkyl glycoside fatty acid polyesters (see Mayer et al; U.S. Pat. No. 4,840,815; Issued Jun. 20, 1989); liquid polyesters of two ether linked hydroxypolycarboxylic acids (e.g. citric or isocitric acid) (see Huhn et al; U.S. Pat. No. 4,888,195; Issued Dec. 19, 1988); liquid polydimethyl siloxanes (e.g., Fluid Silicones available from Dow Corning). Solid nondigestable fats or other solid materials can be added to the liquid nondigestible oils to prevent passive oil loss. Particularly preferred nondigestible fat compositions include those described in U.S. Pat. No. 5,490,995 issued to Corrigan, 1996, U.S. Pat. No. 5,480,667 issued to Corrigan et al, 1996, U.S. Pat. No. 5,451,416 issued to Johnston et al, 1995 and U.S. Pat. No. 5,422,131 issued to Elsen et al, 1995. U.S. Pat. No. 5,419,925 issued to Seden et al, 1995 describes mixtures of reduced calorie triglycerides and polyol polyesters that can be used herein. However the latter composition may provide more digestible fat.

A preferred nondigestible oil is a blend of liquid and solid sucrose fatty acid polyesters. Preferred solid sucrose fatty acid polyesters have saturated and unsaturated fatty acids having from 8 to 24 carbon atoms. These materials and oils are described in U.S. Pat. No. 5,422,131 issued to Elsen or al. (1995) and in U.S. Pat. No. 5,085,884, issued to Young, et al. U.S. Pat. No. 5,306,514 and U.S. Pat. No. 5,306,516 issued to Letton et al. (1994) also describes compositions which can be used herein. These preferred nondigestible oil compositions preferably form into a stiffened material when cooled from a completely melted state to a temperature below 37° C. in a substantially quiescent state (i.e., without agitation). The stiffened material is particularly effective in retaining large quantities of liquid nondigestible oil, and thus inhibiting or preventing passive oil loss of the nondigestible oil through the body of the consumer.

Other suitable polyol fatty acid polyesters are esterified linked alkoxylated glycerins, including those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544.

Additional suitable polyol fatty acid polyesters are esterified epoxide-extended polyols of the general formula $P(OH)_{A+C}(EPO)_N(FE)_B$ wherein P(OH) is a polyol, a is from 2 to about 8 primary hydroxyls, C is from about 0 to about 8 total secondary and tertiary hydroxyls, A+C is from about 3 to about 8, EPO is a $C_3$–$C_6$ epoxide, N is a minimum epoxylation index average number, FE is a fatty acid acyl moiety and b is an average number in the range of greater than 2 and no greater than A+C, as described in U.S. Pat. No. 4,861,613 and EP 0324010 A1, incorporated herein by reference. The minimum epoxylation index average number has a value generally equal to or greater than A and is a number sufficient so that greater than about 95% of the primary hydroxyls of the polyol are converted to secondary to tertiary hydroxyls. Preferably the fatty acid acyl moiety has a $C_7$–$C_{23}$ alkyl chain.

Preferred esterified epoxide-extended polyols for use herein include esterified prepoxylated glycerols prepared by reacting a propoxylated glycerol having from 2 to about 100 oxypropylene units per glycerol with $C_{10}$–$C_{24}$ fatty acids or with $C_{10}$–$C_{24}$ fatty acid esters, as described in U.S. Pat. Nos. 4,983,329 and 5,175,323, respectively, both incorporated herein by reference. Also preferred are esterified propoxylated glycerols prepared by reacting an epoxide and a triglyceride with an aliphatic polyalcohol, as described in U.S. Pat. No. 5,304,665, incorporated herein by reference, or with an alkali metal or alkaline earth salt of an aliphatic alcohol, as described in U.S. Pat. No. 5,399,728, incorporated herein by reference. More preferred are acylated propylene oxide-extended glycerols having a propoxylation index of above about 2, preferably in the range of from about 2 to about 8, more preferably about 5 or above, wherein the acyl groups are $C_8$–$C_{24}$, preferably $C_{14}$–$C_{18}$, compounds, as described in U.S. Pat. Nos. 5,603,978 and 5,641,534, both incorporated herein by reference. Particularly preferred are fatty acid-esterified propoxylated glycerols which exhibit a sharp melt before about 92 F. (33 C.) and have a dilatomeric solid fat index at 92 F. (33 C.) of less than about 30, as described in WO 97/2260, or which have a dilatomeric solid fat index of at least about 50 at 70 F. (21 C.) and at least about 10 at 98.6 F. (37 C.), as described in U.S. Pat. Nos. 5,589,217 and 5,597,605, both incorporated herein by reference.

Other suitable esterified epoxide-extended polyols include esterified alkoxylated polysaccharides. Preferred esterified alkoxylated polysaccharides are esterified alkoxylated polysaccharides containing anhydromonosaccharide units, more preferred are esterified propoxylated polysaccharides containing anhydromonosaccharide units, as described in U.S. Pat. No. 5,273,772, incorporated herein by reference.

In another embodiment of the invention, the high purity lower alkyl esters synthesized according to this invention are advantageously used in linked esterified alkoxylated polyol synthesis methods. Such processes are disclosed in U.S. Pat. Nos. 5,374,446, 5,427,815 and 5,516,544, incorporated herein by reference.

Alkoxylated polyols may be prepared by alkoxylation techniques known in the art such as, for example, reacting a polyol with an epoxide in the presence of a catalyst, such as alkali metal. The alkoxylated polyol may be reacted with linking segments to form a linked alkoxylated polyol. Polycarbonyl linking segments may be selected from acid entities including free acid, acid anhydrides, acid esters, acid halides and mixtures thereof. Polyether glycol linking segment may be selected from polyepoxide-functionalized polyether glycols; as used herein "polyepoxide functionalize" means having two or more epoxide functional groups capable of undergoing ring-opening reactions to form ether bonds. Suitable polyepoxide-functionalized polyether glycols include diepoxide functionalized polyether glycol. The linked alkoxylated polyol may be reacted by transesterification with lower alkyl esters to form a linked esterified alkoxylated polyol.

A suitable process for preparing a linked esterified alkoxylated polyol using high purity lower alkyl esters comprises the steps of converting a source of fatty acids to a product mixture comprising fatty acid lower alkyl esters and by-products; water-washing the product mixture at an elevated temperature and an elevated pressure to remove at least a portion of the by-products from product mixture; fractionally distilling the water-washed product mixture to obtain high purity fatty acid lower alkyl esters having an acid value of no greater than about 1.0; reacting a polyol with an epoxide to form an alkoxylated polyol; reacting the alkoxylated polyol with a linking segment to form a linked alkoxylated polyol; and transesterification of the linked alkoxylated polyol with the high purity fatty acid lower alkyl esters.

Preferred linked esterified alkoxylated polyols are those comprising at least one polyether glycol linking segment, at least two polyol segments each of which is connected to the polyether glycol linking segments either directly or through an unesterified oxyalkylene segment, and at least one fatty acid substituent attached to a polyol segment and selected from fatty acid esters and/or fatty acid esterified oxyalkylene segments, as described in U.S. Pat. No. 5,373,336; those comprising at least one polycarbonyl linking segment, at least two polyol segments each of which is connected to the polycarbonyl linking segments either directly or through an oxyalkylene segment, and at least one fatty acid-esterified oxyalkylene segment attached to a polyol segment, as described in U.S. Pat. No. 5,427,815; or those comprising at least two polycarbonyl linking segments, at least three polyol segments each of which is connected to the polycarbonyl linking segments either directly or through an oxyalkylene segment, and at least one fatty acid-esterified oxyalkylene segment attached to a polyol segment, as described in U.S. Pat. No. 5,516,544. Particularly preferred are linked esterified alkoxylated polyols having a molecular weight greater than 6000 and comprising at least two polycarbonyl linking segment, at least three glyceryl segments and at least one $C_6$–$C_{24}$ fatty acid-esterified oxyalkylene segment attached to a glyceryl segment, as described in U.S. Pat. No. 5,516,544.

By "ester group" is meant a moiety formed from the reaction of a hydroxyl group with an organic acid or acid derivative which moiety contains fatty acid and/or other organic radicals having from 2 to about 26 carbon atoms. Representative examples of such fatty acid and other organic acid radicals include acetic, propionic, butyric, caprylic, capric, lauric, myristic, myristoleic, palmitic, palmitoleic, stearic, oleic, elaidic, riconoleic, linoleic, linolenic, eleostearic, arachidic, arachidonic, behenic, lignoceric, erucic, and cerotic fatty acid radicals and other organic acid radicals including aromatic esters-forming radicals such as benzoic or toluic; branched chain radicals such as isobutyric, neooctanoic or methyl stearic; ultra-long chain saturated or unsaturated fatty acid radicals such as tricosanoic or triconsenoic; cyclic aliphatics such as cyclohexene carboxylic; and polymeric ester-forming radicals such as polyacrylic and dimer fatty acid. The fatty or other organic acid radicals can be derived from naturally occurring or synthetic fatty acids. The acid radicals can be saturated or unsaturated, including positional or geometric isomers, e.g. cis- or trans-isomers, straight chain or branched aromatic or aliphatic, and can be the same for all ester groups, or can be mixtures of different acid radicals.

The term "divalent soap" or "divalent metal soap" shall mean divalent and higher valent (i.e. polyvalent) cation soaps of fatty acids. For a divalent soap such as calcium oleate, there are two-oleic fatty acid chains bound to one calcium ion. For the purpose of identifying the level of divalent metal cations in a composition, all divalent and polyvalent metal cations are assumed to be calcium, and their level in the composition of the present invention are expressed in terms of the equivalent calcium soap. For the purpose of identifying the level of calcium soaps in a composition, all divalent soaps are assumed to be calcium oleate.

As used herein, the term "impurities" is intended to include a variety of constituents which are undesirable in the purified polyol fatty acid polyester product of the present invention. As will be understood, a particular component, e.g. a di- or tri-glyceride, can be an innocuous constituent of a polyol fatty acid polyester product for one application, but, on the other hand, can be undesirable, i.e. an impurity, in another application. For example, because both di- and tri-glyceride are caloric-containing fats, their presence in a polyol fatty acid polyester which is intended for use as a low calorie fat can be undesirable, and, if so, the glycerides would both be considered impurities. Likewise, if the polyol fatty acid polyester is intended for use as a food product, trace amounts of metals would be considered impurities, if said trace amounts of metals are not appropriate for consumption by humans. Items such as breakdown products of an initial reactant which is used to form the polyol fatty acid polyester, (for example, the carmelized by-product of sucrose), can be both inert and suitable for consumption by an average consumer. However, by-products such as the carmelized by-product of a polyol can add undesirable color and/or adversely affect the viscosity of the polyol fatty and polyester product. Thus, the breakdown product of the initial reactant can be considered an impurity even though it is generally inert and consumable. "Impurity", as used herein, is intended to include anything other than the desired polyol fatty acid polyester, the soap and the fatty acid lower alkyl esters, as discussed in greater detail below.

Oil Compositions

It has surprisingly been found that polyol polyesters, in the crude polyol polyester as well as in the final polyol polyester product, can contain a significant level of polyvalent (divalent and higher-valent) metal ions, presumed to be present as metal soaps. The level of divalent metal ions typically found in such polyol polyester products is greater than about 2 ppm. Although it was previously known that divalent soaps are slightly soluble in triglyceride oils in the presence of free fatty acids, it has now been discovered that divalent soaps are much more soluble in nondigestible polyol polyesters than in triglycerides, even when the same amount of free fatty acid is present in the triglyceride and in the polyol polyester. In addition, it has been found that free fatty acid further improves the solubility of the divalent soap in the polyol polyester. Therefore, when converting the divalent soap, it is preferred that the resulting fatty acid radicals of the divalent soaps are converted to mono-valent soaps, which are then easily removed by water washing, etc., as opposed to being converted to free fatty acid, which only solubilize and make the removal of the divalent soaps more difficult.

The reduced calorie cooking and frying oils prepared by the process of the present invention typically contain less than about 530 parts per billion (ppb) divalent and higher valent metal ions, as measured by atomic absorption as described in the Analytical Methods Section hereinafter. Preferably, these reduced calorie cooking and frying oils will contain less than about 340 ppb, and more preferably less than 100 ppb, divalent and higher-valent metal ions. The level of divalent soap is determined and reported based on the level of the metal ion, and does not include the weight of the fatty acid radical of the soap. It is presumed that all the calcium ions, and other divalent metal ions, present in the polyol polyester will complex with free fatty acids that may be present, thereby forming the divalent soaps. This analytical and calculation method is therefore, insensitive to the type (i.e., chain length) of free fatty acids present in the divalent soap.

Cooking and frying oils made as directed herein will have low levels of divalent and higher metal ions; said oils, when further processed or finished according to customary industry practices, (i.e. bleaching, evaporating, and deodorization) will result in cooking and frying oils which typically contain less than about 0.05% (500 parts per million (ppm)) free fatty acids by weight as measured by the Free Fatty Acid Analysis method set forth in the Analytical Methods Section. Preferably, the cooking and frying oils prepared by the process of the present invention contain less than about 0.01% (about 100 ppm), more preferably less than about 50 ppm, and most preferably less than about 10 ppm, free fatty acids.

Ion Exchange Ligands

Preferred ion exchange ligands are capable of effectively chelating and binding the divalent alkali earth metal ions (such as calcium and magnesium), and provide, or are provided with, sufficient alkalinity solution phase has sufficient alkalinity wherein the fatty acid radicals from the divalent soap are converted to monovalent soaps, instead of free fatty acids. Agents which have insufficient alkalinity, such as citric acid, and are not pH adjusted during the process of the invention (for example, with alkali reagent), will liberate free fatty acids; said fatty acids further improve the solubility of any divalent soaps in the polyol polyester, making their removal via ion exchange even more difficult. Consequently, acidic ligands (for example citric acid), without addition of alkali reagents, may chelate and bind some of the divalent metal ions from the divalent soap, but as free fatty acid is liberated, the ability of the citric acid to chelate additional divalent ions is diminished and eventually halted.

Preferred ion exchange ligands are those having a concentration equilibrium constant for $Ca^{++}$ and $Mg^{++}$ ions of at least 2, more preferably of at least 3. Preferred chelates are fully-substituted monovalent salts of citric acid and ethylene diamine tetracetic acid. Other chelates that are effective at ion exchanging to remove divalent ions from divalent soaps include fully-substituted monovalent salts of nitrilotraicetic acid, tripolyphosphate, diethylenetriamine pentaacetic acid, ethylene diamine tetra (methylenephosphonic acid), and diethylenetriamine penta (methylenephosphonic acid). Such ion exchange agents and their concentration equilibrium constant for $Ca^{++}$ and $Mg^{++}$ ions are shown in *Kirk-Othmer,* 3rd Edition, Volume 5, page 348 (Wiley-Interscience, 1979). Preferred monovalent cations for the ion exchange ligands are sodium, potassium, lithium and ammonium salts. Preferably, ion exchange ligands are chelants which can be used in foods and supplements, and are food grade quality.

The preferred ion exchange ligands which are suitable for use in the present invention are those which are in their fully-deprotonated forms in the wash solution, and which have sufficient alkalinity to buffer the ligand wash solution to a pH of at least 6.5 throughout the ion exchanging step.

Ion exchange ligands of the present invention can include monovalent salts of hydroxy acids selected from: glycolic acid, lactic acid, hydroxybutyric acid, glyceric acid, malic acid, tartaric acid, tartonic acid, and citric acid; polycarboxylic acids, such as oxalic acid and malonic acid; metaphosphoric acid, such as phosphoric acid, pyrophosphoric acid, and hexametaphosphoric acid; and ethylene diamine tetraacetic acid; and mixtures thereof. The monovalent salt ions can include sodium, potassium, lithium, and ammonium, and mixtures thereof. Preferred ion exchange ligands can include, for example, tripotassium citrate, trisodium citrate, tetra sodium ethylene diamine tetraacetate ($Na_4EDTA$), and disodium or dipotassium tartrate and malate. The tripotassium citrate is especially preferred for use in the process of the present invention. Also especially preferred are mixtures of trialkali metal citrate and $Na_4EDTA$.

Ion Exchange Process

The process comprises as a first step intimately mixing an aqueous wash solution phase which has an ion exchange ligand with a crude polyol polyester which has a polyvalent soap having a polyvalent ion.

In order to obtain high kinetic rates of dissociation of the ions of the ligand, the ion exchange ligand should be dissolved in an aqueous phase. In addition, the ion exchange ligand is generally insoluble in the polyol polyester oil phase. The process of the present invention requires that the ligand-containing aqueous phase is intimately mixed with the divalent soap-containing polyol polyester oil phase to increase the interfacial surface area between the two phases. It is believed that free fatty acid in the polyol polyester further improves the solubility of the divalent (e.g. calcium) soaps in the polyol polyester. The improved solubility of the divalent soap in the oil phase makes it even more difficult for the ion exchange ligand to react with the divalent soap.

The process comprises a second step of ion exchanging the polyvalent ion from the polyvalent soap to the ion exchange ligand, and forming a monovalent soap. The ion exchange ligand is capable of chelating divalent, particularly alkali earth, metal ions, and is thereby converted to a divalent salt of the ligand. If the reaction occurs in the presence of sufficient alkalinity, the divalent fatty soaps are converted to monovalent soaps. Preferably, the intimate mixing of step a) is continued for a time sufficient to complete the ion exchange of the divalent soap to the monvalent soap.

The ion exchange ligand is added to the crude polyol polyester in an amount sufficient to convert substantially all of the divalent soaps present in the crude polyol polyester to monovalent soaps. Typically, the ion exchange is added at a level ranging from about 0.001% to about 5%. Preferably, the ion exchange is added at a level ranging from about 0.05% to about 2%, more preferably from about 0.05% to about 1% and most preferably from about 0.1% to about 0.5%. Preferably a molar ration of ion exchange ligand to divalent soap of at least 1:1 is used, more preferably a ratio of at least 1:2:1.

To ensure that the calcium soaps are converted to monovalent soaps, as opposed to free fatty acids, ion exchange of the divalent metal ions should occur at a wash solution pH sufficiently high to deprotanate the ion exchange ligand and free fatty acid in the polyol which is contacted by the wash solution. Preferably the pH of the aqueous phase containing the ion exchange ligand will be maintained at about 6.5 and above, more preferably about 7.0 and above, and most preferably about 7.5 and above, during the reacting of the ion exchange ligand with the divalent soap. To promote sufficiently complete conversion to the monovalent soaps it is preferred to maintain the solution pH above the pKa of the free fatty acid, and most preferably at about 1.5 pH units or more above the pKa of the free fatty acid, which is about 5 (See: *Handbook of Biochemistry and Molecular Biology*, 3rd ed., Vol. I, pp. 157–269, CRC Press, Cleveland, Ohio (1976)). An alkali agent can be employed to raise the level of alkalinity, and pH in the wash solution, to the required level. Preferred alkali agents include alkali metal hydroxides, preferably sodium and potassium hydroxide. Such alkali agents are typically added as diluted aqueous solutions.

Preferably, no more than 1% by weight of the fatty acid radicals in the polyol polyester is comprised as free fatty acid. Most preferably, there is a negligible (substantially none)level of free fatty acid remaining in the polyol polyester.

The process of the present invention comprises the third step of removing the polyvalent ion exchange ligand, the monovalent soap, and other aqueous soluble impurities, from the treated polyol polyester. Methods for removing the polyvalent ion exchange ligand and the monovalent soap include aqueous washing, filtration, centrifugation, and combinations thereof. Preferred is a water washing method of removing these materials from the polyol polyester. The water washing method requires that the washing solution and the treated polyol polyester be intimately mixed in order to increase the interfacial surface area between the two phases, to maximize the mass transfer of the monovalent soap to the aqueous wash solution. The process methods and apparatus used for water washing of the treated polyol polyester are similar to those process methods and apparatus used for the intimate mixing of the aqueous ion exchange solution and the crude polyol polyester of the first step.

In a preferred process, the same process method and apparatus is used for conducting all three process steps of the invention.

In accordance with the present process of the invention, an unrefined polyol fatty acid polyester and the aqueous ion exchange solution are fed into a mixing and reacting vessel. As used herein "mixing vessel" and "reacting vessel" include any conventional tank, column or other process equipment and/or vessel which allows the solutions to contact one another intimately. Single stage columns, multistage columns, batch tanks, static mixers and bubble columns are examples of suitable mixing vessels and other appropriate mixing vessels, and combinations thereof, are known to those skilled in the art.

A multistage column with agitation is a preferred mixing and reacting vessel for the process described herein. Both co-current and counter-current processes are practical for the multistage columns. However, a co-current operation is less efficient than counter-current with respect to the use of water, although co-current columns are generally easier to scale-up than counter-current columns. Once inside the column, the ion exchange wash solution and the unrefined polyol fatty acid polyester are agitated, creating an intimate mixture which is sufficiently controlled to avoid the formation of stable emulsions. The intimate mixing of the two phases is continued for a time sufficient to convert the divalent soaps to the monovalent soaps. In addition, the intimate mixing should also continue for a time sufficient for other impurities, including color bodies, to mass transfer from the treated polyol polyester phase to the aqueous wash solution phase. Subsequently, the aqueous wash solution phase and the treated polyol polyester phase are made to separate into two phases. The treated polyol polyester phase is then further refined to produce the final polyol polyester product.

The process, as well as the polyol polyester and wash solution components, is generally conducted at a temperature which maintains the polyol polyester in a liquid state. When the nondigestible oil contains solid oil (having a complete melt point above bout 37° C.), higher temperatures will be necessary to keep the solid oil in a molten or liquid state.

In a preferred process system, the mixture of treated polyol fatty acid polyester and used ion exchange wash solution in the mixing vessel is preferably maintained at a temperature of from about 20° C. to about 100° C., more preferably from about 40° C. to about 95° C., and most preferably from about 65° C. to about 90° C. The mixing vessel can be operated at subatmospheric, atmospheric or superatmospheric pressures. One benefit to operating at superatmospheric pressure is that the temperature of the mixture can be increased slightly since the increase in pressure raises the boiling point of the constituents. Higher temperatures can be useful to maximize the solubility of the resulting monovalent soap, divalent salt of the ligand, and other impurities in the ion exchange wash solution, thus maximizing the purity of the treated polyol fatty acid polyester. In this way, the mixing vessel can be operated at higher temperatures without boiling the constituents. When solid polyol polyester components are present, it is generally necessary to maintain the temperature of the feed stocks and of the process at a temperature sufficiently high to maintain the solid polyol polyester in a molten state, throughout the processing of the nondigestible oil.

The benefits of operating the mixing vessels described herein at reduced or increased pressure must be weighted against the additional equipment and operational costs required with operating at other than atmospheric conditions. Thus, for purposes of efficiency and economics, it is preferred to operate the mixing vessels described herein at atmospheric pressure.

Often, it is desirable to premix the wash solution and the crude polyol fatty acid polyester prior to introducing them into the mixing vessel. The use of one inlet stream comprising a pre-mix of crude polyol fatty acid and the ion exchange wash solution can provide manufacturing convenience and economic advantage over feeding the two streams separately to the mixing vessel.

After the ion exchange wash solution and the crude polyol fatty acid polyester are fed into the mixing vessel, they are dispersed to a level sufficient to produce a shear rate which results in the formation of an intimate mixture, yet avoids the formation of a stable emulsion. The mixture, as discussed above, typically contains droplets of one solution dispersed in the other solution. Preferably, the mixture comprises droplets of the wash solution in the polyol polyester phase. Preferably, the droplets have an average diameter within the range of from about $5\mu$ to about $3000\mu$, more preferably about $5\mu$ to about $70\mu$, and most preferably about $5\mu$ to about $20\mu$. The composition of the mixture will largely depend on the mass flow rates of each solution fed into the mixing vessel, as is discussed in greater detail below.

The dispersion will depend on, among other process parameters, the size and design of the mixing vessel, the mass flow rate of the solutions fed into the mixing vessel and the type and amount of agitation. "Agitation", as used herein includes any means for producing the mixture of wash solution and crude polyol fatty acid polyester. Agitation can be provided by a variety of commonly used processes and types of equipment. For example, impellers and rotating discs can be used to provide dynamic agitation, while forced gas (i.e. "bubbling"), static mixers and pulsation of the feed stream can provide acceptable non-dynamic agitation of the mixture in the mixing vessel. Agitation by impellers is preferred for use with the mixing vessels described herein, though it is understood that other methods of agitation are also suitable for use in the claimed methods.

As can be appreciated, when impellers are used for agitation, their speed and design are important in promoting mixing and mass transfer of impurities from the treated polyol fatty acid polyester to the wash solution. By dispersing the mixture sufficiently to produce a shear rate which avoids the formation of stable emulsions, reaction of the ion exchange ligand with divalent soaps, and subsequent mass transfer of impurities and monovalent soap from the unrefined polyol fatty acid polyester to the wash solution can be optimized. As discussed above, other forms of agitation are appropriate for use with the present invention as long as the agitation is sufficient to produce a shear rate which avoids the formation of stable emulsions and simultaneously forms a dispersion containing the claimed droplet sizes.

The residence time of the mixture within the mixing vessel is also important in maximizing the extent of reaction of the ion exchange ligand with divalent soaps, and subsequent mass transfer of impurities from the unrefined polyol fatty acid polyester to the wash solution. Preferred residence times of the mixture in the mixing vessel are within the range of from about 0.5 minutes to about 30 minutes, more preferably from about 1 minute to about 15 minutes, and most preferably from about 1 minute to about 10 minutes, and can be selected depending upon, for example, the concentration of impurities and emulsifier soap in the crude and/or treated polyol fatty acid polyester being fed in to the mixing vessel, the level of divalent soap to be treated and removed, as well as the tolerable level of impurities and monovalent soap in the treated polyol polyester product.

If the mixing vessel is a column, the number of stages in the column will necessarily affect the residence time as well as the amount of purification that occurs. Selection of the appropriate number of stages will depend on the height and diameter of the column, flow rates of each stream, and the method and amount of agitation, along with other process parameters. When the unrefined polyol polyester and the wash solution are fed co-currently, it is preferred that the column has from about 1 stage to about 7 stages, preferably from about 5 to about 7 stages. When the unrefined polyol polyester and the wash solution are fed counter-current, it is preferred that the column has from abut 5 stages to about 25 stages.

Another process parameter which can be varied to improve the reaction of he ion exchange ligand with divalent soaps, and subsequent mass transfer of monovalent soap and impurities from the polyol fatty acid polyester to the wash solution, is the amount of ion exchange wash solution fed into the column. A preferred ratio of the mass feed rate of polyol fatty acid polyester to the mass feed rate of the ion exchange wash solution is in the range of from about 2:1 to about 50:1, more preferably from about 3:1 to abut 50:1, and most preferably from about 4:1 to 20:1. More specifically, the ratio of the mass feed rate of polyol fatty acid polyester to the mass feed rate of the wash solution fed to a co-current multistage column is preferably in the range of from about 3:1 to about 20:1, and the ratio of the mass feed rate of polyol fatty acid polyester to the mass feed rate of the ion exchange wash solution fed to a counter current multistage column is preferably in the range of from about 4:1 to about 40:1.

As is discussed above, preferred mixing vessels for use with the present invention are multistage columns with agitation. Multistage columns suitable for use with the present invention include, but are not limited to, rotary disc contractors. Oldshue-Rushton extractors, Scheibel extraction towers, Kuhni towers, and the like. These columns are discussed by Perry, et al. *Chemical Engineers Handbook,* 6th Edition, 1984, pages 21–77 to 21–79, incorporated herein by reference. The columns in Perry et al. are schematically shown with counter current flow. A heavy liquid is fed from the top of a vertical column and removed from the bottom with a light liquid fed near the bottom and extracted near the top. As was discussed above, the two streams of the present invention can be fed counter current, i.e., the streams flow through the column in opposite directions, or co-current, i.e., both streams flow through the column in the same direction. When the two streams are fed at or near the same end of the column, they are normally removed at or near the opposite end of the columns.

Baffles can be provided between stages within the column wherein the size and shape of the opening in the baffle is designed to provide the desired residence time within each stage and other process conditions. Likewise, within each stage, an impeller can be provided, and typically the impellers are connected to a single shaft which runs through the column. Thus, one shaft can drive all of the impellers, maintaining the agitation speed relatively constant within different stages. However, as can be appreciated, impellers with independent drive motors and/or gears can be provided at individual stages or between stages so that the respective impeller speeds vary from one stage to the next. Agitation speed within the column and within individual stages, the size and shape of the baffle openings separating stages and the number of stages are all design criteria which can be varied to achieve a desired purification.

Multistage columns can be provided with "calming" zones at one or both ends of the column wherein the treated mixture (that is, the resulting mixture following sufficient shear rate and residence time to achieve the desired degree of mass transfer of impurities from the polyol to the wash solution) is not agitated and can separate into two phases. If a calming zone is provided, the two phases can then be separated through the use of two extraction ports, i.e., a first port for extracting the first phase and a second port for extracting the second phase.

When the mixing is completed, the mixture is made to separate into two phases due to the general immiscibility between the oil phase containing the purified polyol fatty acid polyester and the aqueous wash solution phase containing the monovalent soap, the divalent salt of the ligand, and other water soluble impurities.

All droplets diameters reported herein were measured using a Lasentech scanning laser light detector. More specifically, the Lasentech instrument is a focused beam reflectant measurement system which consists of a computer interface, a laser diode, detectors, a 10 meter fiber optic cable, and a measuring probe. The light from the laser diode travels down the fiber optic cable to the probe. The light is focused to a very small point in the probe through a sapphire window into the material of interest. When the light beam passes over a particle, or droplet in this case, light is scattered in the backward direction. This light is collected and is passed back to the field unit where it starts a clock. When the light has passed over the droplet, the backscattering stops and this stops the clock. By knowing the speed of the light beam and the length of the backscattering pulse, the diameter of the droplet can be determined. For a given set of conditions, the average droplet diameter is calculated by dividing the sum of all the diameters by the number of droplets measured. As will be understood, the unrefined polyol fatty acid polyester can conventionally be produced by the reaction of a polyol with a fatty acid lower alkyl ester. However, the unrefined polyol fatty acid polyester can be provided from any available source or production method employed in the art. The purified polyol fatty acid polyester can be used as, among other things, a low calorie fat in foods and, in fact, the purified polyol fatty acid polyester of the present invention is particularly advantageous for use as a food additive owing to its improved purity.

The wash solution comprises a solvent which will be generally immmiscible with the polyol polyester to easily separate the two phases, and will be a solvent for the ion exchange ligand. Non-limiting examples of a wash solution solvent are water, methanol, acetone, and ethyl actate. Water and, more generally, aqueous-based wash solutions, are preferred for use in the processes described herein due to availability and cost, but it is understood that other solvents are appropriate for use with the processes and methods described herein if the solvents, when mixed with the unrefined polyol fatty acid polyester under the conditions described herein, remove at least a portion of the impurities from the unrefined polyol fatty acid polyester Fatty acid lower alkyl ester is often reacted with a polyol to form a polyol fatty acid polyester. In such reactions, a stoichiometric excess of fatty acid lower alkyl ester is typically used to completely esterify the polyol. The residual fatty acid lower alkyl ester remaining in the reaction product is not normally soluble in water which is a preferred solvent of the present invention. Additionally, since the fatty acid lower alkyl ester is a feed stock in the reaction of a polyol to form a polyol fatty acid polyester, it is desirable to collect and recycle the residual fatty acid lower alkyl ester. Thus, fatty acid lower alkyl ester is generally not included within the meaning of the term "impurities" as defined herein. A more detailed description of the direct recycle of lower alkyl esters can be found in the Provisional patent application Ser. No. 08/797,018 (Attorney Docket 6508), entitled "Lower Alkyl Eser Recycling in Polyol Fatty Acid Polyester Synthesis", and is hereby incorporated by reference herein.

Fatty acid lower alkyl ester cannot normally be removed by contact with an aqueous based wash solution alone, although small amounts of both the fatty acid lower alkyl ester and the desired polyol fatty acid polyester can be unavoidably entrained in the wash solution. Fatty acid lower alkyl esters are preferably removed from the polyol fatty acid polyester by thermal evaporation. However, the lower alkyl ester evaporates at a lower temperature than does the polyol fatty acid polyester, and any impurities which have boiling points less than the boiling point of the polyol fatty acid polyester may be evaporated along with the lower alkyl ester. To produce a lower alkyl ester of sufficient purity for direct recycle into the polyol fatty acid polyester production process, it is often desirable to remove as much of the monovalent soap and impurities as possible using the water washing methods of the present invention prior to the evaporation step.

A preferred emulsifier for use in the transesterification reaction of a polyol to form a polyol fatty acid polyester is alkali metal fatty acid soap. As used herein, the term "emulsifier soap" means the alkali metal salts of saturated and unsaturated fatty acids having from about eight to about twenty-four carbon atoms, which are added to the transesterification reaction of the polyol polyester. Accordingly, suitable emulsifier soaps include, for example, the lithium, sodium, potassium, rubidium, and cesium salts of fatty acids such as capric, lauric, myristic, palmitic, linoleic, oleic, and stearic acids, as well as mixtures thereof. A mixture of fatty acid derived from soybean oil, sunflower oil safflower oil, cottonseed oil, palm oil and corn oil is preferred for use herein. An especially preferred emulsifier soap is, for example, the potassium soap made from palmitic acid and stearic acid. In addition to alkali metal soap, other emulsifiers such as sucrose fatty acid mono-, di- and tri-esters can be used. Solid mono- and di-glycerides can also be used, although they are less preferred.

While an emulsifier, in general, and an emulsifier soap, specifically, are often desirable reaction components, they are generally undesirable in the polyol fatty acid polyester product. It is desirable to remove substantially all of the emulsifier soap and monovalent soap from the reaction product prior to the thermal evaporation of excess methyl ester to minimize color degradation during evaporation. Additionally, the presence of emulsifier soap in substantial quantities, i.e. greater than about 2000 ppm, can cause processing difficulties in the form of stable emulsions between the ion exchange wash solution and the unrefined polyol fatty acid polyester. It is preferred that the concentration of emulsifier soap in the unrefined polyol fatty acid polyester be below about 2000 ppm, more preferably, below about 1000 ppm and most preferably, below about 500 ppm, to avoid the formation of such stable emulsions. Additionally, as will be discussed in greater detail below, the treated polyol fatty acid polyester, i.e., the polyol fatty acid polyester leaving the mixing vessel described herein, can be further treated by bleaching and/or filtration to further reduce the level of monovalent soap and emulsifier soap below detection limits, i.e., below about 50 ppm. The level of soap in a polyol fatty acid polyester can be measured by a neutralization titration using HCl, or other strong acid, to a predetermined endpoint.

A base initiator, also known at a basic catalyst, in generally used to allow the transesterification reaction of a polyol to form a polyol fatty acid polyester to occur at temperature below the degradation temperature of the polyol. Though basic catalyst is a preferred reaction component, it is generally considered an impurity in the polyol fatty acid polyester product stream. Discussions of the types of basic catalysts and their function in the transesterification of polyols can be found in U.S. Pat. No. 3,963,699 to Rizzi et al., and U.S. Pat. Nos. 4,517,360 and 4,518,772 to Volpenhein, which discussions are incorporated herein by reference. The basic catalyst is typically a strong base with an affinity for hydrogen and is often referred to as a base initiator because it serves to transform the polyol from a stable molecule to a reactive ion. Thus, the terms "basic catalyst" and "base initiator" are interchangeable as used herein. Specifically, the basic catalyst removes a hydrogen from the polyol molecule resulting in a polyol ion which is in a reactive state. For example, the basic catalyst converts sucrose to sucrate ion. Preferred basic catalysts are carbonate and methoxide ions, which can be complexed with an alkali or alkaline earth metal, for example, potassium or sodium.

As used herein, the phrase "phase transfer catalyst" is intended to include all chemical species which can interact with a polyol to form a chemical complex, wherein the complexed polyol can travel from one phase to a second phase, and wherein the uncomplexed polyol would not normally be soluble in the second phase. A phase transfer catalyst, as described herein, is to be distinguished from an emulsifier, e.g., a fatty acid soap, in that an emulsifier is believed to provide a single phase in which both chemical species are soluble, i.e. without the need for chemical complexing. As was the case with the other reaction components discussed above, a phase transfer catalyst and any breakdown product resulting therefrom, while often desirable in the transesterification of a polyol to form a polyol fatty acid polyester, is generally considered an impurity in a polyol fatty acid polyester product.

Having discussed the various solutions and process equipment suitable for use with the processes described herein, the next step is the post-treatment processing of the mixture. As used herein, "treated" is intended to mean the process of removing at least a portion of impurities and/or soap from the polyol fatty acid polyester. Hence, "treated polyol fatty acid polyester" means the polyol fatty acid polyester resulting when at least a portion of the impurities and soap have been removed by the processes described herein. Preferably, the treated mixture is removed from the mixing vessel and allowed to settle and separate due to the forces of gravity into the two phases. Each of the two phases can then be separately removed as a treated polyol fatty acid polyester phase and an impurity- and monovalent soap-containing wash solution. Other methods of separation are equally appropriate and can be preferred in certain cases. For example, if time is a major consideration and capital and/or operational costs are not, the treated mixture can be transferred from the mixing vessel to a centrifuge where it can be separated into a light phase, which will normally comprise the treated polyol fatty acid polyester, and a heavy phase, which will normally comprise the impurity- and soap-containing wash solution.

While the use of other suitable ion exchange ligands also provide some small levels of color quality improvement of the crude polyol polyester, it has been surprisingly found that the use of alkali metal citrate as the ion exchange ligand in the wash solution also provides a substantial improvement in the color quality of the polyol polyester (i.e. lighter color). Consequently, it is highly preferred to use of alkali metal citrate, or the use of citric acid or mono- or di-alkali metal citrates in combination with alkali reagents, to raise the alkalinity and pH of the wash solution.

The treated polyol fatty acid polyester can contain a small amount of the ion exchange wash solution along with residual impurities and monvalent soap, while the ion exchange wash solution can contain a small amount of the polyol fatty acid polyester and other organic oils. It is preferred that the treated polyol fatty acid polyester contains less than about 1% by weight of the total of wash solution and impurities, including less than about 100 ppm monovalent soap, and more preferably less than about 50 ppm monovalent soap. It is preferred that the ion exchange wash solution contain not greater that about 5 weight percent of organic oil. Since residual impurities, monovalent soap and wash solution can remain in the treated polyol fatty acid polyester after being treated in the mixing vessel, the treated polyol fatty acid polyester can be further refined in additional purification steps. For example, the treated polyol fatty acid polyester can be vacuum dried to remove residual ion exchange wash solution and volatile impurities. Particulate silica can also be contacted with the polyol fatty acid polyester to remove particulate impurities and monovalent soap. Preferably, the treated polyol fatty acid polyester is vacuum dried prior to the removal of the excess fatty acid lower alkyl esters so that the concentration of wash solution, monovalent soap and impurities is less than 0.1% by weight. Additionally, as was discussed above, thermal evaporation to remove excess fatty acid lower alkyl esters, if any are present, can be employed with is often desirable.

Product Uses

The polyol polyesters which comprised the frying oils prepared by the process of the present invention can optimally be blended with conventional triglyceride oils. As used herein, the term "triglyceride oil" refers to those triglyceride compositions which are fluid or liquid above about 25° C. Although not a requirement, the triglyceride oils useful in the present invention can include those which are fluid or liquid below 25° C. These triglyceride oils consist primarily of triglyceride materials, but can also include residual levels of other components such as mono- and diglycerides. To remain fluid or liquid at temperatures below 25° C., the triglyceride oil contains a minimal amount of glycerides having melting points higher than about 25° C. so as to limit the solids increase when the triglyceride oil is cooled. It is desirable that the triglyceride oil be chemically stable and resistant to oxidation.

Suitable triglyceride oils can be derived from naturally occurring liquid vegetable oils such as cottonseed oil, soybean oil, safflower oil, corn oil, olive oil, coconut oil, palm kernel oil, peanut oil, rapeseed oil, canola oil, (i.e., rapeseed oil low in erucic acid), sesame seed oil, sunflower seed oil, and mixtures thereof. Also suitable are liquid oil fractions obtained from palm oil, lard and tallow by, for example, graining or directed interesterification, followed by separation of the oils. Oils predominantly in glycerides of unsaturated acids can need some hydrogenation to maintain flavor, but care should be taken not to greatly increase the amount of glycerides melting above 25° C. When oils are selected which have a larger amount of solids melting between 25° C. and 40° C. than are desirable, it can be necessary to separate out the solids. For example, refined and slightly hydrogenated soybean oil is suitable, as well as refined cottonseed oil.

Typically, the cooking and the frying oils of the present invention contain from 0% to about 90% triglyceride fat or oil. Preferably, the cooking and frying oils of the present invention contain from about 0 to about 70% triglyceride oil, more preferably from about 1 to about 30% triglyceride oil and most preferably from 1 to about 10% triglyceride oil.

In preparing the reduced calorie cooking and frying oils described in the present invention, the nondigestible polyol polyesters are typically blended with an optional triglyceride oil after the divalent and higher soaps have been removed from the polyol polyester as described herein before. Optionally, the triglyceride oil can be separately treated in a manner as herein before described the polyol polyesters to remove divalent metal soaps from the triglycerides before the triglyceride is blended with the polyol polyester (although divalent soaps are much less soluble in triglyceride oils than in polyol polyesters, and therefore, are present at much lower levels). Alternatively, the nondigestible polyol polyester and the triglyceride oil can be blended together first, and the blend can be treated as herein before described to remove the divalent soaps from the blend.

ANALYTICAL METHODS
A. Free Fatty Acid Analysis
1. Weigh approximately 15.0 grams of test sample into a clean 250 ml beaker.
2. Add stir bar, 30 ml of ethanol and 15 drops of phenolphthalein solution into beaker.
3. While stirring mixture, titrate with 0.1 N NaOH solution until a light pink color persists for 30 seconds.
Free Fatty Acid Calculation
Percent free fatty acid (as oleic acid)=mls of 0.1 N NaOH×2.82/ sample weight (grams).
B. Lovibond Color Management
1. Using Lovibond Automatic Tiniometer, calibrate instrument to AOCS specifications using 2.9R/12Y standard.
2. Warm 5¼" sample cuvette and chamber to 120° F.
3. Place filled cuvette into instrument and read color (AOCS Lovibond).

The instrument used was the Lovibond Automatic Tintometer. It was pre warmed to 70°
C. The instrument was calibrated using the AOCS calibration standard (i.e., 2.9R/12Y). Samples were prepared by either warming to 70° C. and measuring directly or by first filtering the sample through Whathman 40 filter paper under nitrogen, warming to 70° C. then measuring. The paper removes particles which interfere with the color measurements. For this reason filtered samples tend to give a truer measure of visible color.

Both the 5.25" and 1" sample cuvettes are used. Color measurements between cuvettes are not directly proportional. Therefore, it is important to keep data comparisons consistent (i.e., filtered/1" cell is different than unfiltered/1" cell which is different than filtered/5.25" cell).
C. Divalent and Higher Valent Metal Ion and Soap Analysis
Method EPA SW846 (herein incorporated by reference) is to be used to analyze a sample of nondigestible fat for quantitative levels of metal ions, including alkali earth metal such as $C^{++}$ and $Mg^{++}$, and transition metals such as $Fe^{++}$. All divalent and polyvalent metal ions are assumed to be calcium ions on an equal molar basis.

The Detailed Description can be better understood when read in conjunction with the following example, wherein polyol fatty acid polyesters containing divalent soaps are reacted with ion exchange ligands in a wash solution and the resultant monovalent soaps removed to purify the polyol polyester. Product color resulting from color bodies is measured using a commercially available Lovibond color analyzer.

EXAMPLES

EXAMPLE 1

A crude sucrose polyester, typical of crude sucrose polyester made to produce Olean™ (manufactured by The Proctor and Gamble Company, Cincinnati, Ohio), is prepared according to the general two-stage process described in U.S. Pat. No. 3,963,699 to Rizzi, et al., assigned to The Procter & Gamble Company, issued Jun. 16, 1976. Said crude sucrose polyester contains approximately about 75.4% octaester and approximately about 6.2% soap, is reacted in five successive and substantially identical batches of approximately about 3900 pounds each. The individual batches are reacted in two stages and each batch has the following composition.

|  | BATCH ONE Stage 1 | BATCH TWO Stage 1 |
|---|---|---|
| Cottonseed oil methyl esters | 1306 lbs. (592 kgs) | 1305 lbs. (592 kgs) |
| soap | 200 lbs. (90.8 kgs) | 200 lbs. (90.8 kgs) |
| sucrose | 300 lbs. (136 kgs) | 300 lbs. (136 kgs) |
| tri-potassium carbonate | 2.4 lbs. (1.09 kgs) | 2.4 lbs. (1.09 kgs) |
|  | Stage 2 | Stage 2 |
| Cottonseed oil methyl esters | 2093 lbs. (950 kgs) | 2090 lbs. (949 kgs) |
| tri-potassium carbonate | 2.4 lbs. (1.09 kgs) | 2.4 lbs. (1.09 kgs) |
|  | BATCH THREE Stage 1 | BATCH FOUR Stage 1 |
| Cottonseed oil methyl esters | 1310 lbs. (595 kgs) | 1306 lbs. (595 kgs) |
| soap | 200 lbs. (90.8 kgs) | 200 lbs. (90.8 kgs) |
| sucrose | 300 lbs. (136 kgs) | 200 lbs. (90.8 kgs) |
| tri-potassium carbonate | 2.4 lbs. (1.09 kgs) | 2.4 lbs. (1.09 kgs) |
|  | Stage 2 | Stage 2 |
| Cottonseed oil methyl esters | 2091 lbs. (949 kgs) | 2091 lbs. (949 kgs) |
| tri-potassium carbonate | 2.4 lbs. (1.09 kgs) | 2.4 lbs. (1.09 kgs) |
|  | BATCH FIVE Stage 1 |  |
| Cottonseed oil methyl esters | 1305 lbs. (592 kgs) |  |
| soap | 200 lbs. (90.8 kgs) |  |
| sucrose | 300 lbs. (136 kgs) |  |
| tri-potassium carbonate | 2.4 lbs. (1.09 kgs) |  |
|  | Stage 2 |  |
| Cottonseed oil methyl esters | 2094 lbs. (951 kgs) |  |
| tri-potassium carbonate | 2.4 lbs. (1.09 kgs) |  |

Each of the five batches is purified according to the following procedure: Each reaction batch is individually washed with a small amount of water (about 1 weight part water for 5.5 weight parts crude sucrose polyester) to hydrate and flocculate the monovalent soap, and is then centrifuged to remove most of the precipitated soaps (to a level of about 447 ppm) and particular catalyst as a sludge. The washed, unbleached sucrose polyester (pH of about 7:1) is then placed into three identical stirred stainless steel tanks in substantially equal amounts, and is then washed with a chelant water wash solution to deliver a tri-potassium citrate concentration of 4975 ppm in the crude sucrose polyester. The chelate water wash solution contains 3400 lbs. of water and 97.42 lbs. of potassium citrate and has a pH of 8.59. 970 lbs. of this solution is added to each of the tanks. The sucrose polyester and chelant wash solutions are agitated at about 185–190° F. for 10 minutes; after stopping agitation for 5 minutes, the solutions are again agitated for an additional 5 minutes. After settling for 1.5 hours, the water layer is removed. To each of the three tanks of the treated sucrose polyester is added 66 pounds of silica gel. The contents of the three tanks of the treated successively passed through a filter, forming a filter cake of the silica gel.

The treated sucrose polyester has the following levels of calcium, free fatty acid, and product color, respectively: 540 ppb, 0.22% and 0.83.

Typical commercial production of Olean™ made without the chelant was solution process of the present invention contains about 2200 ppb to 2800 ppb calcium metal ions and would have a Lovibond red index of approximately 2.3.

What is claimed is:

1. A process for preparing a nondigestible polyol polyester having improved stability against hydrolysis, the process comprising the steps of:
   a. intimately mixing an aqueous wash solution phase comprising an ion exchange ligand with a crude polyol polyester comprising a divalent soap having a divalent ion,
   b. ion exchanging the divalent and higher valent ion from the divalent and higher valent soap to the ion exchange ligand, to form a divalent and higher valent ion exchange ligand,
   c. forming a monovalent soap, and
   d. removing the divalent and higher valent ion exchange ligand and the monovalent soap from the treated polyol polyester,
   whereby the level of divalent and higher valent metal ions in the resulting nondigestible polyol polyester is reduced.

2. The process of claim 1 wherein level of divalent and higher valent metal ions is reduced to less than about 550 ppb divalent and higher valent metal ions.

3. The process of claim 1 wherein the aqueous wash solution is maintained at a pH of about 6.5 or above during ion exchange step b.

4. The process of claim 2 wherein the level of divalent and higher valent metal ions is reduced to less than about 340 ppb.

5. The process of claim 1 wherein the level of divalent and higher valent metal ions is reduced to less than about 100 ppb.

6. The process according to claim 1 wherein the resulting nondigestible polyol polyester has less than about 500 ppm free fatty acids.

7. The process according to claim 6 wherein the resulting nondigestible polyol polyester has less than about 100 ppm free fatty acids.

8. The process according to claim 7 wherein the resulting nondigestible polyol polyester has less than about 50 ppm free fatty acids.

9. The process according to claim 1 wherein the ion exchange ligand is contained in an amount of from about 0.05% to about 2% by weight of the mixture in step A.

10. The process according to claim 1 wherein the ion exchange ligand is a tri-alkali metal citrate salt, tartaric acid, ethylene diamine tetraacetic acid, or mixtures thereof.

11. The process according to claim 10 wherein the ion exchange ligand is selected from tri-potassium citrate, tri-sodium citrate, and mixtures thereof.

12. The process of claim 1 wherein in step (d) the monovalent soap and the divalent ion exchange ligand are removed from the treated polyol polyester using a process selected from water washing, filtering, centrifuging, and combinations thereof.

13. The process according to claim 11 wherein the resulting nondigestible polyol polyester contains less than abut 100 ppm free fatty acid, less than 340 ppb divalent and higher valent metal ions, and has a Lovibond red color of less than about 2.

14. The process according to claim 13 wherein the resulting nondigestible polyol polyester contains less than about 50 ppm free fatty acid, less than 100 ppb divalent and higher valent metal ions, and has a Lovibond red color of less than about 2.

15. The process according to claim 3 wherein the ion exchange ligand is selected from the group consisting of di-alkali metal citrate, mono-alkali metal citrate, citric acid, and mixtures thereof, and wherein the pH of the aqueous wash solution is adjusted with an alkali agent.

16. The process according to claim 15 wherein the alkali metal is selected from sodium, potassium, and mixtures thereof.

17. The process according to claim 16 wherein the pH of the aqueous wash solution is adjusted with alkali metal hydroxide.

18. A nondigestible polyol polyester composition having improved stability against hydrolysis, comprising a nondigestible polyol polyester and less than about 550 ppb of divalent and higher valent metal ions.

19. The nondigestible polyol polyester according to claim 18, further comprising less than about 500 ppm free fatty acid.

20. A nondigestible polyol polyester according to claim 19 comprising less than about 340 ppb divalent and higher valent metal ions, and less than about 100 ppm free fatty acid.

21. A nondigestible polyol polyester according to claim 20 comprising the less than about 100 ppb divalent and higher valent metal ions, and less than about 50 ppm free fatty acid.

22. A nondigestible polyol polyester according to claim 19 having a Lovibond red color of less than about 6.

23. A nondigestible polyol polyester according to claim 19 having a Lovibond red color of less than about 4.

24. A nondigestible polyol polyester according to claim 20 having a Lovibond red color of less than about 2.

25. A nondigestible polyol polyester according to claim 21 having a Lovibond red color of less than about 1.0.

26. A nondigestible polyol polyester according to claim 18 wherein the polyol is sucrose.

27. A nondigestible polyol polyester according to claim 18 wherein the polyol is alkoxylated glycerin.

* * * * *